United States Patent [19]

Liu et al.

[11] 4,283,493
[45] Aug. 11, 1981

[54] PROCESS OF PRODUCING ANTIBIOTIC X-14766A BY A STREPTOMYCES

[75] Inventors: Chao-Min Liu; John Westley, both of Cedar Grove, N.J.

[73] Assignee: Hoffmann-La Roche Inc., Nutley, N.J.

[21] Appl. No.: 128,992

[22] Filed: Mar. 10, 1980

Related U.S. Application Data

[62] Division of Ser. No. 944,825, Sep. 22, 1978, Pat. No. 4,221,724.

[51] Int. Cl.³ .............................................. C12P 17/18
[52] U.S. Cl. .................................. 435/119; 435/118; 435/886
[58] Field of Search ................................ 435/118, 119

[56] References Cited

PUBLICATIONS

Juslen et al., The Journal of Antibiotics, Sep. 1978, pp. 820–828, vol. 31, No. 9.
Westley, The Journal of Antibiotics, vol. 32, No. 9, pp. 959–960, Sep. 1979.

*Primary Examiner*—Lionel M. Shapiro
*Attorney, Agent, or Firm*—Jon S. Saxe; Bernard S. Leon; Frank P. Hoffman

[57] ABSTRACT

A compound of the formula

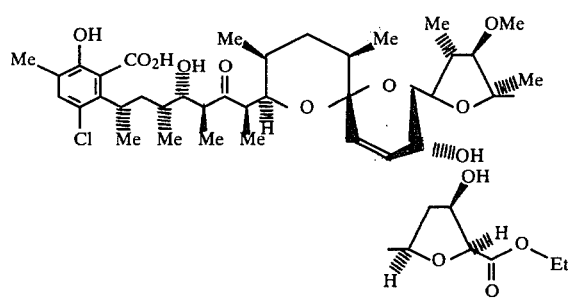

and its pharmaceutically acceptable salts are disclosed.

The compound exhibits antibacterial activity, antimalarial activity, has activity as a growth promotant for ruminants and as an agent in the treatment of swine dysentery. Also provided is a process to produce the novel compound.

1 Claim, No Drawings

PROCESS OF PRODUCING ANTIBIOTIC X-14766A BY A STREPTOMYCES

This is a division of application Ser. No. 944,825, filed Sept. 22, 1978, now U.S. Pat. No. 4,221,724, issued Sept. 9, 1980.

DESCRIPTION OF THE INVENTION

The present invention relates to a novel polyether ionophore antibiotic of the formula

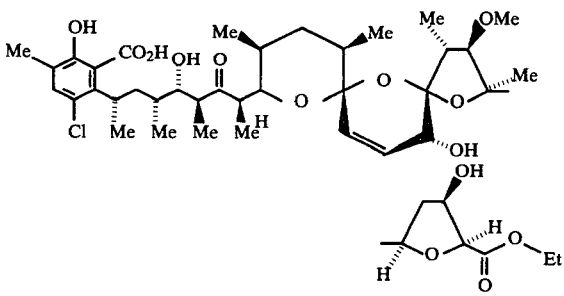

and its pharmaceutically acceptable salts.

The shorthand expression Me and Et are utilized above to represent methyl and ethyl respectively.

This compound agent and its salts exhibit activity as an antibacterial agent, for the control of swine dysentery, or antimalarial agent and as a growth promotant for ruminants.

Antibiotic X-14766A is the designation given to a crystalline antibiotic produced by a Streptomyces organism isolated from a sample of soil collected at Playa Blanca, Mexico. Lyophilized tubes of the culture bearing the laboratory designation X-14766 were deposited with the United States Department of Agriculture, Agricultural Research Service, Northern Regional Research Laboratories (NRRL), Peoria, Ill. The culture, given the identification number NRRL 11335 by NRRL has been made available to the public through NRRL.

Antibiotic X-14766A is a polyether antibiotic and forms a variety of pharmaceutically acceptable salts. These salts are prepared from the free acid form of the antibiotic by methods well-known for compounds of the polyether type in the art; for example, by washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Examples of organic bases forming pharmaceutically acceptable salts with the polyether compounds are lower alkyl amines, primary, secondary and tertiary hydroxy-lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water-solubility which makes them amenable to parenteral use.

MORPHOLOGICAL CHARACTERISTICS

The representative strain of Streptomyces X-14766 has the following characteristics:

Sodium chloride tolerance, hydrolysis of casein and reduction of nitrate were determined by the methods recommended by Gordon and Smith, J. Bacteriol., 66, 41–48, 1953. Starch hydrolysis was determined after growth on agar of Actinomyces broth (Difco) with 0.25% soluble starch, and was tested by flooding the plates with iodine-KI solution. Gelatin hydrolysis was tested according to Skerman, (A Guide to Identification of the Genera of Bacteria, The Williams and Wilkins Co., Baltimore, Md. 1967) using Actinomyces broth (Difco) with 2% agar in place of meat infusion agar. All tests were run at 28° C.

The standard ISP media of Shirling and Gottlieb were used for the description of growth and pigmentation (color determinations were made after two weeks of incubation at 28° C.). Carbon utilization was also determined by the method of Shirling and Gottlieb (Int. J. Syst. Bacteriol., 16, 313–340, 1966). A 24 hour old ISP-1 broth culture was homogenized and centrifuged to obtain a washed suspension for inoculation. The ability of the organism to grow at 10°, 28°, 37°, 45° and 50° C. was investigated by inoculating broth of ISP-1 (Difco) medium. Cell wall analysis was performed by the method of Becker et al. (Applied Microbiol. 12, 421–423, 1964).

MICROSCOPIC EXAMINATION

Strain X-14766 produces a substrate mycelium, which does not fragment into spores, and an aerial mycelium which eventually forms spore chains. After 14 days of incubation at 28° C., the spore chains appear spira in form with 15 to 20 spores per chain. Spores are spiny and range in size form $1.2 \times 1.0$ μm to $1.1 \times 0.73$ μm. The cell wall of this organism contains the LL-isomer of diaminopimelic acid. These characteristics place this organism in the genus Streptomyces (Lechevalier et al., Adv. Appl. Microbiol., 14, 47–72, 1971).

MACROSCOPIC EXAMINATION

Table 1 summarizes the amount of growth, degree of sporulation, spore mass color and color of reverse substrate mycelium of culture X-B 14766 on various solid media.

TABLE 1

| | Cultural Characteristics of Strain X-14766 | | |
|---|---|---|---|
| Agar medium | Amount of growth; Degree of Sporulation | Spore mass color[a] | Color of reverse-substrate mycelium[a] |
| Yeast malt extract (ISP-2)[b] | abundant growth; well sporulated | 2ih (dark covert gray) mostly; 2fe (covert gray) at edge | 2ge (covert tan) mostly; 2li (covert brown) |
| Oatmeal (ISP-3)[b] | abundant growth; well sporulated | 3fe (silver gray) | 2ec (biscuit) |

TABLE 1-continued

Cultural Characteristics of Strain X-14766

| Agar medium | Amount of growth; Degree of Sporulation | Spore mass color[a] | Color of reverse-substrate mycelium[a] |
|---|---|---|---|
| Inorganic salts starch (ISP-4)[b] | moderate growth; well sporulated; hydrolyzes starch | 2fe (covert gray); edges of b (oyster white) | 2gc (bamboo), trace of 1½ie (lt. olive) |
| Glycerol asparagine (ISP-5)[b] | moderate growth; moderate sporulation | 2dc (natural string) | 2gc (bamboo) |
| Czapek-Dox[c] | moderate growth; sparse sporulation | 2dc (natural string) | 2ie (light mustard tan) |

[a]The color scheme used was that taken from the Color Harmony Manual, 4th ed., 1958 (Container Corporation of America, Chicago).
[b]Media recommended by the International Streptomyces Project (Shirling and Gottlieb, Int. J. System Bacteriol. 16, 313-340 1966).
[c]Czapek-Dox broth (BBL) to which 1.5% agar was added.

TABLE 2

Carbon Utilization by Strain X-14766
Growth response* of:

| Carbon Source | X-14766 |
|---|---|
| D-Glucose | ++ |
| D-Xylose | + |
| L-Arabinose | ++ |
| L-Rhamnose | ++ |
| D-Fructose | ++ |
| D-Galactose | +(+) |
| Raffinose | − |
| D-Mannitol | ++ |
| i-Inositol | ++ |
| Salicin | ± |
| Sucrose | ++ |
| Cellulose | |

*−, Negative response; +, doubtful response; +, more growth than on carbon control but less than on glucose; +(+), growth slightly less than the amount on glucose, ++, positive response equal to the amount of growth on glucose.
**Physiological Characteristics: Table 2 reports the results of carbon utilization tests by strain X-14766 and Table 3 lists diagnostically important properties.

TABLE 3

Metabolic and Morphological Characteristics of Strain X-14766

| Test | X-14766 |
|---|---|
| ISP-6 darkening | + |
| Melanin, ISP-7 | variable |
| Casein hydrolysis | + |
| Gelatin hydrolysis | ± |
| Starch hydrolysis | + |
| NaCl (%) tolerance | −5 |
| Growth range temp (°C.) | 28–45 |
| ISP-1 darkening | + |
| Reverse-side pigment | none |
| Soluble pigment | none |
| Antibiotic production | X-14766A |
| Nitrate reduction | − |
| Hygroscopic property | variable |
| Spore chain form/ # spores per chain | spira/15–20 |
| Spore surface | spiny |

A comparison of the description of strain X-14766 with those of the Streptomyces species described in Bergey's Manual (Buchanan and Gibbons, ed., Bergey's Manual of Determination Bacteriology, 8th ed., 748–829, 1974), H. Nonomura's key for classification (J. Ferment. Technol., 52, 78–92, 1974) and Pridham and Lyons' classification (Dev. Ind. Microbiol. 10, 183–221, 1969), showed that no known species are identical to X-14766 based on the following combination of criteria: gray spore mass color, spiral spore chain form, spiny spore surface, chromogenic reaction on ISP media, 1, 6 and 7, and carbon utilization characteristics. *Streptomyces malachitorectus* and *S. malachitofuscus* resemble X-14766 based on carbon utilization data. Culture X-14766 is closest to *S. malachitofuscus* because of a further similarity in a negative nitrate reduction. Slight differences in spore ornamentation (spiny for X-14766 and spiny/- hairy for *S. malachitofuscus*) and the property of production of a unique antibiotic, X-14766A, justifies our considering X-14766 as a variety of *S. malachitofuscus*, which we named *S. malachitofuscus* subsp. *downeyi*.

The Streptomyces X-14766 described herein includes all strains of Streptomyces which form a compound as claimed in the present application and which cannot be definitely differentiated from the strain NRRL 11335 and its subcultures including mutants and variants. The claimed compound is described herein and after this identification is known, it is easy to differentiate the strains producing this compound from others.

Streptomyces X-14766 when grown under suitable conditions, produces an antibiotic X-14766A. A fermentation broth containing Streptomyces X-14766 is prepared by inoculating spores or mycelia of the organism producing the antibiotic into a suitable medium and then cultivating under aerobic conditions. For the production of the antibiotic, cultivation on a solid medium is possible for production in large quantities, cultivation in a liquid medium is preferable. The temperature of cultivation may be varied over a wide range, 20°–35° C., within which the organism may grow but a temperature of 26°–30° C. and a substantially neutral pH are preferred. In the submerged aerobic fermentation of the organism for the production of antibiotic X-14766A, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of antibiotic X-14766A.

Antibiotic X-14766A has a toxicity ($LD_{50}$) in mice of 350 mg/kg (po) and 5.75 mg/kg (ip).

The antibiotic activity of the antibiotic X-14766A is shown by the following table:

TABLE 4

| Organism | | Minimum Inhibitory Concentration (μg/ml) |
|---|---|---|
| Staphylococcus aureus | ATCC 6538P | 0.2 |
| Sarcina lutea | ATCC 9341 | 0.2 |
| Bacillus sp. E | ATCC 27859 | 0.04 |
| Bacillus subtilis | NRRL 558 | 0.2 |
| Bacillus megaterium | ATCC 8011 | 0.08 |
| Bacillus sp. TA | ATCC 27860 | 0.08 |
| Mycobacterium phlei | ATCC 355 | 0.2 |
| Streptomyces cellulosae | ATCC 3313 | 0.2 |

As is indicated above, antibiotic X-14766A and its salts possess the property of adversely affecting the growth of certain Gram-positive bacteria. It is useful in wash solutions for sanitary purposes as in the washing of hands and the cleaning of equipment, floors or furnishings of contaminated rooms or laboratories. It is useful also for suppressing the growth of sensitive organisms in plate assays and other microbiological media.

Antibiotic X-14766A has also exhibited antimalarial activity with an $ED_{50}$ of 2.5 mg/kg against *Plasmodium bergei* in mice.

In vitro activity against anaerobic bacteria has also been exhibited by the antibiotic as shown below.

TABLE 5

| Organism | | Minimum Inhibitory Concentration* (μg/ml) |
|---|---|---|
| Bacteroides fragilis | ATCC 12290 | 0.195 |
| Clostridium histolyticum | 503-86 | 0.0098 |
| Clostridium septicum | 503-34 | 0.0098 |

*Two-fold serial broth dilution tests were carried out using trypticase soy broth (TSB, BBL) as the test medium. All tests were incubated at 37° C. overnight under anaerobic conditions.

Antibiotic X-14766A also exhibited in vitro anticoccidial activity against *Eimeria tenella* at 0.1 ppm.

Testing for activity against *Treponema hyodysenteriae*, a cause of swine dysentery consisted of inoculation of blood agar plates containing a series of two and fourfold dilutions of antibiotic X-14766A and ipronidazole, an agent used in the treatment of swine dysentery, with tenfold dilutions of each of the *T. hyodysenteriae* strains (H 78, H 140, H 179). After 48 hours of incubation at 42° C. in an anerobic atmosphere, Minimum Inhibitory Concentrations were recorded as the lowest concentrations of compound which completely inhibited the most dilute inoculum of each *T. hyodysenteriae* strain. The results which show X-14766A's superior activity are as follows:

TABLE 6

| Method of T. hyo Inoculation | Antibiotic X-14766A | | | Ipronidazole | | |
|---|---|---|---|---|---|---|
| | T. hyo Strains (MIC) | | | | | |
| | B78 | B140 | B179 | B78 | B140 | B179 |
| Steers | <0.04 | <0.04 | <0.04 | 0.16 | 0.16 | 0.16 |
| Steers | <0.04 | <0.04 | <0.04 | 0.16 | 0.16 | 0.31 |
| Steers | 0.02 | 0.04 | 0.02 | 0.31 | 0.31 | 0.31 |
| Syringe | 0.02 | 0.02 | — | 0.63 | 0.63 | — |
| Syringe | 0.04 | 0.04 | — | 0.63 | 0.63 | — |
| Syringe | 0.04 | 0.04 | — | 0.63 | 0.63 | — |

Administration of antibiotic X-14766A hereafter "Antibiotic" or "Antibiotic Compound" prevents and treats ketosis as well as improves feed utilization in ruminants or swine. The causative mechanism of ketosis is a deficient production of propionate compounds. A presently recommended treatment is administration of propionate acid or feeds which preferentially produce propionates. It is obvious that encouraging propionate production from ordinary feeds will reduce incidence of ketosis.

It has been found that antibiotic X-14766A increases the efficiency of feed utilization in ruminant animals when it is administered orally to the animals. The easiest way to administer the antibiotic is by mixing it in the animal's feed.

However, the antibiotic can be usefully administered in other ways. For example, it can be incorporated into tablets, drenches, boluses, or capsules, and dosed to the animals. Formulation of the antibiotic compound in such dosage forms can be accomplished by means of methods well known in the veterinary pharmaceutical art.

Capsules are readily produced by filling gelatin capsules with any desired form of the desired antibiotic. If desired, the antibiotic can be diluted with an inert powdered diluent, such as a sugar, starch, or purified crystalline cellulose in order to increase its volume for convenience in filling capsules.

Tablets of the antibiotic are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used. Commonly used absorbents again include starch and lactose while magnesium carbonate is also useful for oily substance. Frequently used binders are gelatin, gums, starch, dextrin and various cellulose derivatives. Among the commonly used lubricants are magnesium stearate, talc, paraffin wax, various metallic soaps, and polyethylene glycol.

The administration of the antibiotic compound may be as a slow-pay-out bolus. Such boluses are made as tablets except that a means to delay the dissolution of the antibiotic is provided. Boluses are made to release for lengthy periods. The slow dissolution is assisted by choosing a highly water-insoluble form of the antibiotic. A substance such as iron filing is added to raise the density of the bolus and keep it static on the bottom of the rumen.

Dissolution of the antibiotic is delayed by use of a matrix of insoluble materials in which the drug is imbedded. For example, substances such as vegetable waxes, purified mineral waxes, and water-insoluble polymeric materials are useful.

Drenches of the antibiotic are prepared most easily by choosing a water-soluble form of the antibiotic. If an insoluble form is desired for some reason, a suspension may be made. Alternatively, a drench may be formulated as a solution in a physiologically acceptable solvent such as a polyethylene glycol.

Suspensions of insoluble forms of the antibiotic can be prepared in nonsolvents such as vegetable oils such as peanut, corn, or sesame oil, in a glycol such as propylene glycol or a polyether glycol; or in water, depending on the form of the antibiotic chosen.

Suitable physiologically acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants serve to suspend the antibiotic. For example, lecithin, alkylphenol polyethylene oxide adducts, naphthalenesulfonates, alkylbenzesulfonates, and the polyoxyethylene sorbitan esters are useful for making suspensions in liquid nonsolvents.

In addition many substances which affect the hydrophilicity, density, and surface tension of the liquid can assist in making suspensions in individual cases. For example, silicone anti-foams, glycols sorbitol, and sugars can be useful suspending agents.

The suspendable antibiotic may be offered to the grower as a suspension, or as a dry mixture of the antibiotic and adjuvants to be diluted before use.

The antibiotic may also be administered in the drinking water of the ruminants. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with the antibiotic compound is by the formulation of the compound into the feed supply. Any type of feed may be medicated with the antibiotic compounds, including common dry feeds, liquid feeds, and pelleted feeds.

The methods of formulating drugs into animal feeds are well-known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound, or of premix, in the feed.

All of the methods of formulating, mixing and pelleting feeds which are normally used in the ruminant feed art are entirely appropriate for manufacturing feeds containing the antibiotic compound.

As has been shown, oral administration of the antibiotic beneficially alters the production of propionates relative to the production of acetates in the rumen. It may therefore be postulated that the same treatment would also benefit monogastric animals which ferment fibrous vegetable matter in the cecum since it would be expected that a beneficial change in the propionate/acetate ration would occur upon oral administration of the instant antibiotic. Horses, swine and rabbits are exemplary animals which digest a part of their food by cecal fermentation.

DETERMINATION OF VOLATILE FATTY ACID PRODUCTION

A bovine, surgically modified with a rumen fistula, is used as a source of rumen fluid. The integrity of the rumen is maintained by a rumen cannula (Bar Diamond Labs, Parma, Idaho) which is opened in order to obtain rumen fluid samples. The animal is fed twice daily an 80% concentrate (AHRES ration #39):20% roughage ration. The rumen fluid is obtained prior to the A.M. feeding. The rumen fluid is strained through 4 layers of cheesecloth into a 1 gallon Nalgene container and is kept under anaerobe quality $CO_2$. One thousand mls of the strained rumen fluid are added to 2000 mls of an ice cold buffer based upon that specified by Cheng et al., J. Dair. Sci., 38, 1225 (1955). The composition of this buffer is as follows:

| $Na_2HPO_4$ | 0.316 g/l | $MgSO_4$ | 0.112 |
| $KH_2PO_4$ | 0.152 | $CaCl_2$ | 0.038 |
| $NaHCO_3$ | 2.260 | $FeSO_4 . 7H_2O$ | 0.008 |
| $NaCl$ | 0.375 | $ZnSO_4 . 7H_2O$ | 0.004 |
| $KCl$ | 0.375 | $CuSO_4 . 5H_2O$ | 0.002 |

The buffered rumen fluid is held in a 4 liter separatory funnel. In order to help maintain the anaerobic character of the rumen fluid and the homogeneity of the buffered rumen fluid, anaerobe quality $CO_2$ is bubbled constantly through the fluid in a separatory funnel beginning approximately ½" above the separatory funnel stopcock.

Two hundred and fifty ml Erlenmeyer flasks are used for individual fermentations. Each flask to which a compound will be added contains one gram of a finely ground 80% concentrate:20% alfalfa hay ration. Flasks which are to be used as drug-free controls contain 1.07 grams of the finely ground ration. One ml of test compound dissolved in an apropriate solvent is added to each flask and allowed to sit for ½ to 1 hour. Each compound is examined in duplicate flasks at a final concentration of 50 ppm. Solvent without test compound is added to drug-free control fermentation flasks. Monensin at 10 and 50 ppm is used as a positive control in all fermentations.

Eighty grams of buffered rumen fluid are added to each flask containing test compound and 85.93 grams are added to control flasks. Flasks to which all components have been addded are stoppered with a gas collection apparatus and left sitting at room temperature until all flasks have been completed. Six ml samples are withdrawn from all control flasks as the 0 time samples. The incubation period and the collection of gas evolved during fermentation is initiated 10 minutes after the flasks have been placed in a 38° C. water bath. Flasks are incubated with shaking (90 oscillations per minute) for 4 hours.

The volume of gas produced by each fermentation is measured at ½ hour intervals. The manometric apparatus for collection of gas and measurement of the volume evolved has been described by Trei et al., J. Anim. Sci., 30, 825 (1970).

Rumen fluid is poured into 25×150 mm glass tubes and left in an ice bath for approximately 15 minutes to permit settling of particulate matter. The 6 ml quantity of rumen fluid is then added to a 2 ml quantity of 25% (W/V) metaphosphoric acid (JT Baker) in 13 ml polycarbonate centrifuge tubes (Autoclear, IEC). Each tube is stoppered and thoroughly mixed. Tubes are left in an ice bath for 30 minutes and then centrifuged at 16,000 rpms for 10 minutes in an 874 angle head in an IEC B20 centrifuge. A 1 ml quantity of the internal standard (0.25% 2-methyl valeric acid, Aldrich Chemical Company) is then added to a 4 ml quantity of the supernate. The resulting mixture is filtered through a 0.22 micron Millipore filter using a Swinnex filter and a 5 ml syringe.

The filtrate is sealed in one ml glass vials with Teflon lined rubber crimp septa.

Each vial, representing each of the individual fermentations, is analyzed for volatile fatty acids.

Each vial is analyzed with three consecutive injections. Concentrations of acetate, propionate, i-butyrate, n-butyrate, i-valerate and n-valerate are calculated by comparison with analyses of a standard solution of VFA's using an internal standardization method.

The results are stated in the following table:

TABLE 1

Effect of miscellaneous ionophores on gas and VFA production in in vitro rumen fermentations.

| Compound | Compound Concentration (ppm) | Percent Production of Control Fermentations | | |
|---|---|---|---|---|
| | | Total VFA(%) | Rate of Gas Production | $C_3/C_2 + nC_4$ |
| X-14766A | 50 | 150.1 | 90 | 0.501 |
| | 10 | 138.7 | 89 | 0.488 |
| Monensin | 50 | 105.3 | 89 | 0.565 |
| | 10 | 110.7 | 85 | 0.575 |
| Narasin | 50 | 106 | 86 | 00.583 |
| | 10 | 102.5 | 88 | 0.581 |
| Salinomycin | 50 | 146.9 | 83 | 0.497 |
| | 10 | 145.5 | 90 | 0.512 |
| Control | 0 | 100 | 100 | 0.349 |

EXAMPLE 1

Shake flask fermentation of Streptomyces X-14766

The X-14766A producing culture is grown and maintained on an Amidex agar slant having the following composition (grams/liter distilled water):

| | |
|---|---|
| Amidex | 10.0 |
| N-Z amine A | 2.0 |
| Beef extract | 1.0 |
| Yeast extract | 1.0 |
| $CoCl_2 \cdot 6H_2O$ | 0.02 |
| Agar | 20.0 |

The slant is inoculated with Streptomyces X-14766 culture and incubated at 28° C. for 7 to 14 days. A chunk of agar containing the sporulated culture from the agar slant is then used to inoculate a 500-ml Erlenmeyer flask containing 100 ml sterilized inoculum medium having the following composition (grams/liter distilled water):

| | |
|---|---|
| Tomato pomace dried solids | 5.0 |
| Distillers solubles | 5.0 |
| OM peptone paste | 5.0 |
| Debittered yeast | 5.0 |
| Corn starch | 20.0 |
| $CaCO_3$ | 1.0 |
| $K_2HPO_4$ | 1.0 |

Adjust pH to 7.0 with NaOH before sterilization.

The inoculated inoculum medium is incubated at 28° C. for 72 hours on a rotary shaker, operating at 250 rpm with a 2-inch stroke.

A 3 ml portion (3% v/v) of the resulting culture is then used to inoculate a 500-ml Erlenmeyer flask containing 100 ml sterilized production medium having the following composition (grams/liter distilled water):

| | |
|---|---|
| Glucose | 10.0 |
| Edible molasses | 20.0 |
| HySoy T* | 5.0 |
| $CaCO_3$ | 2.0 |

*soybean meal, Hunko Sheffield Chemical Co., Lyndhurst, N.J.

Adjust pH to 7.2 before autoclaving.

The inoculated medium is incubated at 28° C. for 5 days on a rotary shaker running at 250 rpm with a 2-inch stroke.

EXAMPLE 2

Tank fermentation of Streptomyces X-14766

The X-14766A producing culture is grown and maintained on an Amidex agar slant having the following composition (grams/liter distilled water):

| | |
|---|---|
| Amidex* | 10.0 |
| N-Z amine | 2.0 |
| Beef extract | 1.0 |
| Yeast extract | 1.0 |
| $CoCl_2 \cdot 6H_2O$ | 0.02 |
| Agar | 20.0 |

*Modified starch, Corn Products

The slant is inoculated with Streptomyces X-14766 culture and incubated at 28° C. for 7 to 15 days. A chunk of agar from the sporulated culture is then used to prepare vegetative inoculum by inoculating a 500-ml Erlenmeyer flask containing 100 ml of inoculum medium having the following composition (grams/liter distilled water):

| | |
|---|---|
| Tomato pomace dried solids | 5.0 |
| Distiller soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 | pH is adjusted to 7.0 before autoclaving.

The inoculated medium is incubated for 72 hours at 28° C. on a rotary shaker operating at 250 rpm with a 2-inch stroke.

Twenty ml (1%, v/v) of this culture are used to inoculate a 6-liter Erlenmeyer flask containing 2 liters of inoculum medium having the following composition (grams/liter distilled water):

| | |
|---|---|
| Tomato pomace dried solids | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 | pH is adjusted to 7.0 before autoclaving at 15 to 20 pound pressure for 45 minutes.

The inoculated medium is incubated for 72 hours at 28° C. on a rotary shaker operating at 250 rpm.

Four liters of this culture are used to inoculate 60 gallons of the following production medium in a 100 gallon fermentor (grams/liter tap water):

| | |
|---|---|
| Tomato pomace dried solids | 5.0 |

| -continued | |
|---|---|
| Distillers dried solubles | 5.0 |
| OM peptone | 5.0 |
| Debittered yeast | 5.0 |
| Corn starch | 20.0 |
| $CaCO_3$ | 1.0 |
| $K_2HPO_4$ | 1.0 |
| Sag 4130 Antifoam (Union Carbide) | 0.1 |

The pH of the medium is adjusted to 7.0 with NaOH before sterilization for 1¼ hours with 60 lb/in² steam.

The inoculated medium is aerated with compressed air at a rate of 3 cubic feet per minute, and is stirred with agitators at 280 rpm. The fermentation is carried out at 28° C. for 5 days.

EXAMPLE 3

1. Isolation of the sodium salt:

2-[7-[2-[(5-Ethoxycarbonyl)-tetrahydro-4-hydroxyfuran-2-yl]-15-hydroxy-3-methoxy-2,4,10,12-tetramethyl-1,6,8-trioxadispiro[4.1.5.3] pentadec-13-en-9-yl]-4-hydroxy-1,3,5,7-tetramethyl-6-oxoheptyl]-3-chloro-6-hydroxy-5-methylbenzoic acid sodium salt (antibiotic X-14766A-sodium salt) (anhydrous).

The whole broth (60 gallons) from the 116 hour fermentation of Streptomyces sp. X-14766 was extracted with 60 gallons of ethyl acetate at the harvest pH (7.6). The solvent layer was separated and concentrated under reduced pressure to an oil weighing approximately 80 grams. The oil was dissolved in 0.32 liters of n-hexane and extracted twice with equal volumes of acetonitrile. The pooled extracts were concentrated under reduced pressure to an oil (53 grams), dissolved in 1.2 liters of diethyl ether, and washed sequentially with 0.32 liters of 1 N HCl, water, saturated sodium carbonate, and water. The solvent layer was dried over sodium sulfate and concentrated under reduced pressure. After the addition of n-hexane crystalline X-14766A was recovered by filtration. The crude crystals were recrystallized by dissolving in 42 ml of methylene chloride, washing again with 1 N HCl; and saturated sodium carbonte, decolorizing with DARCO G-60 and finally concentrating with the additional of n-hexane to give analytically pure X-14766A sodium salt.

m.p. 219°, $[\alpha]_D -4.7°$ (cl, $CHCl_3$); Calc.: $C_{43}H_{62}ClO_{14}Na$ (861.38): C. 59.95; H. 7.26; CL. 4.12; Na. 2.67. Found: C. 60.30; H. 7.27; Cl. 4.25; Na. 2.15.

EXAMPLE 4

2. Free acid form of antibiotic X-14766A

2-[7-[2-[(5-Ethoxycarbonyl)-tetrahydro-4-hydroxyfuran-2-yl]-15-hydroxy-3-methoxy-2,4,10,12-tetramethyl-1,6,8-trioxadispiro[4.1.5.3] pentadec-13-en-9-yl]-4-hydroxy-1,3,5,7-tetramethyl-6-oxoheptyl]-3-chloro-6-hydroxy-5-methylbenzoic acid, hydrate.

A solution of the sodium salt of X-14766A in ethyl acetate was washed with N HCl to remove the sodium cation, and the solvent removed under reduced pressure. Crystallization from acetonitrile yielded the free acid form of antibiotic X-14766A as a monohydrate.

m.p. 160°, $[\alpha]_D -11.3°$ (cl, $CHCl_3$), $-15°$ (cl, methanol). Free acid, monohydrate: $C_{43}H_{63}ClO_{14} \cdot H_2O$ (857.40); Calc. C. 60.24; H. 7.64; Cl. 4.13; O. 27.99; $H_2O$. 2.10; Found C. 60.92; H. 7.88; Cl. 3.42; O. 27.99; $H_2O$. 1.97.

EXAMPLE 5

3. Thallium salt of antibiotic X-14766A

2-[7-[2-[(5-Ethoxycarbonyl)-tetrahydro-4-hydroxyfuran-2-yl]-15-hydroxy-3-methoxy-2,4,10,12-tetramethyl-1,6,8-trioxadispiro[4.1.5.3] pentadec-13-en-9-yl]-4-hydroxy-1,3,5,7-tetramethyl-6-oxoheptyl]-3-chloro-6-hydroxy-5-methylbenzoic acid thallium salt.

To a solution of the free acid form of antibiotic X-14766A in ethyl acetate was added saturated aqueous thallium hydroxide. After thorough mixing, the thallium salt was isolated from the organic phase by evaporation under reduced pressure and crystallization from n-hexane/ethanol to give crystals of $C_{43}H_{62}ClO_{14}Tl$.

m.p. 194°-196°, $[\alpha]_D +29°$ (cl, $CHCl_3$); Microanalysis Calc. C. 49.53; H. 5.99; Cl. 3.40; Tl. 19.58; Found C. 50.03; H. 6.02; Cl. 3.42; Tl. 17.87.

EXAMPLE 6

| TABLE FORMULATION: - (Wet Granulation) | | | | |
|---|---|---|---|---|
| Item | Ingredient | mg/tablet | mg/tablet | mg/tablet | mg/tablet |
| 1. | X-14766A | 1 | 5 | 10 | 25 |
| 2. | Lactose | 202 | 232 | 261 | 280 |
| 3. | Modified starch | 25 | 35 | 45 | 55 |
| 4. | Pregelatinized starch | 20 | 25 | 30 | 35 |
| 5. | Distilled water q.s. | — | — | — | — |
| 6. | Magnesium stearate | 2 | 3 | 4 | 5 |
| | Weight of tablet | 250 mg | 300 mg | 350 mg | 400 mg |

PROCEDURE:
1 Mix Items 1-4 in a suitable mixer.
2 Granulate with sufficient distilled water to proper consistency. Mill.
3 Dry in a suitable oven.
4 Mill and mix with magnesium stearate for 3 minutes.
5 Compress on a suitable press equipped with appropriate punches.

EXAMPLE 7

| TABLET FORMATION: - (Direct Compression) | | | | |
|---|---|---|---|---|
| Item | Ingredient | mg/tablet | mg/tablet | mg/tablet | mg/tablet |
| 1. | X-14766A | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
| | Weight of tablet | 300 mg | 300 mg | 300 mg | 300 mg |

PROCEDURE:
1 Mix Item 1 with equal amount of lactose. Mix well.
2 Mix with Item 3, 4, and remaining amount of item 2. Mix well.
3 Add magnesium stearate and mix for 3 minutes.
4 Compress on a suitable press equipped with appropriate punches.

EXAMPLE 8

| CAPSULE FORMULATION: | | | | |
|---|---|---|---|---|
| Item | Ingredients | mg/capsule | mg/capsule | mg/capsule | mg/capsule |
| 1. | X-14766A | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2.0 | 2.5 |

-continued
CAPSULE FORMULATION:

| Item | Ingredients | mg/capsule | mg/capsule | mg/capsule | mg/capsule |
|---|---|---|---|---|---|
| | Capsule fill weight | 250 mg | 350 mg | 400 mg | 450 mg |

PROCEDURE:

1 Mix Items 1, 2, 3 and 5 in a suitable mixer. Mill.

2 Add talc and mix well.

3 Encapsulate on suitable equipment.

What is claimed:

1. A process to produce a compound of the formula

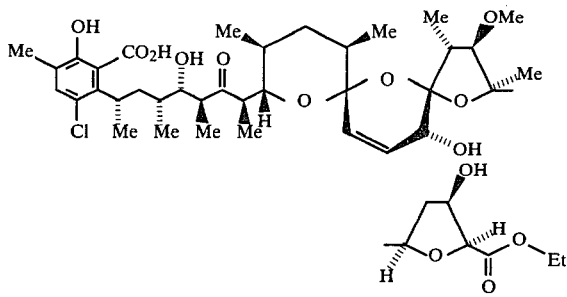

which comprises:

cultivating a strain of Streptomyces X-14766A, NRRL 11335 in an aqueous carbohydrate solution containing a nitrogenous nutrient under submerged aerobic conditions and thereafter isolating the X-14766A antibiotic from said solution.

* * * * *